(12) United States Patent
Kim

(10) Patent No.: US 8,410,256 B2
(45) Date of Patent: Apr. 2, 2013

(54) NUCLEIC ACID APTAMER WHICH SPECIFICALLY BINDS TO BISPHENOL A

(75) Inventor: So Youn Kim, Seoul (KR)

(73) Assignee: Dongguk University Industry-Academic Cooperation Foundation, Seoul (KR)

( * ) Notice: Subject to any disclaimer, the term of this patent is extended or adjusted under 35 U.S.C. 154(b) by 0 days.

(21) Appl. No.: 13/201,797

(22) PCT Filed: Feb. 16, 2010

(86) PCT No.: PCT/KR2010/000951
§ 371 (c)(1),
(2), (4) Date: Sep. 29, 2011

(87) PCT Pub. No.: WO2010/093222
PCT Pub. Date: Aug. 19, 2010

(65) Prior Publication Data
US 2012/0015354 A1    Jan. 19, 2012

(30) Foreign Application Priority Data
Feb. 16, 2009   (KR) .................. 10-2009-0012286

(51) Int. Cl.
 C07H 21/04 (2006.01)
 C07H 21/02 (2006.01)
 C12Q 1/68 (2006.01)
(52) U.S. Cl. .................. 536/23.1; 435/6.1; 997/704
(58) Field of Classification Search .................. None
See application file for complete search history.

(56) References Cited

U.S. PATENT DOCUMENTS

| 2003/0064530 A1* | 4/2003 | Okada et al. .................. 436/514 |
| 2005/0214823 A1* | 9/2005 | Blume et al. .................. 435/6 |

FOREIGN PATENT DOCUMENTS

| KR | 10-0828481 B1 | 5/2008 |
| WO | WO 2009/102438 | * 8/2009 |

OTHER PUBLICATIONS

Yeon Seok Kim et al., NICE, 2008, pp. 690-695, vol. 26, No. 6.

* cited by examiner

*Primary Examiner* — Richard Schnizer
(74) *Attorney, Agent, or Firm* — Rabin & Berdo, P.C.

(57) ABSTRACT

A nucleic acid aptamer capable of binding specifically to bisphenol A and a method of detecting and removing bisphenol A using the nucleic acid aptamer. The nucleic acid aptamer capable of binding specifically to bisphenol A has affinity for bisphenol A at nM concentration, and thus can detect even a very small amount of bisphenol A. Also, the nucleic acid aptamer can specifically detect only bisphenol A without showing affinity for other bisphenols, including bisphenol B having no difference from bisphenol A except for a single methyl group. Accordingly, the nucleic acid aptamer is effective in detecting and removing the environmental hormone bisphenol A which is difficult to detect by conventional methods.

8 Claims, 6 Drawing Sheets

Bisphenol A (●), negative control (○) immobilization in Sol-gel chip

Assay with cy3 labeled aptamer #3

SEQUENCE LISTING

```
<160> NUMBER OF SEQ ID NOS: 41

<210> SEQ ID NO 1
<211> LENGTH: 15
<212> TYPE: DNA
<213> ORGANISM: Artificial
<220> FEATURE:
<223> OTHER INFORMATION: bisphenol A aptamer

<400> SEQUENCE: 1
cctgagkwac tgycc                                                    15

<210> SEQ ID NO 2
<211> LENGTH: 18
<212> TYPE: DNA
<213> ORGANISM: Artificial
<220> FEATURE:
<223> OTHER INFORMATION: bisphenol A aptamer

<400> SEQUENCE: 2
atcgartkcc cscggccg                                                 18

<210> SEQ ID NO 3
<211> LENGTH: 58
<212> TYPE: DNA
<213> ORGANISM: Artificial
<220> FEATURE:
<223> OTHER INFORMATION: bisphenol A aptamer

<400> SEQUENCE: 3
gccgttggtg tggtgggccy agggccggcg gcgcacagct gttatagacg yctccagc     58

<210> SEQ ID NO 4
<211> LENGTH: 60
<212> TYPE: DNA
<213> ORGANISM: Artificial
<220> FEATURE:
<223> OTHER INFORMATION: bisphenol A aptamer
```

```
<400> SEQUENCE: 4
tgacggtggc gtggagggcg cgtatcaatc gttgatcgca gggccgtcat accgktsgrg    60

<210> SEQ ID NO 5
<211> LENGTH: 34
<212> TYPE: DNA
<213> ORGANISM: Artificial
<220> FEATURE:
<223> OTHER INFORMATION: bisphenol A aptamer
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (11)..(11)
<223> OTHER INFORMATION: n is a, c, g, or t
<220> FEATURE:
<221> NAME/KEY: misc_feature
<222> LOCATION: (13)..(14)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t
<220> FEATURE:
<221> NAME/KEY: misc_feature
<222> LOCATION: (26)..(26)
<223> OTHER INFORMATION: n is a, c, g, or t
<220> FEATURE:
<221> NAME/KEY: misc_feature
<222> LOCATION: (33)..(33)
<223> OTHER INFORMATION: n is a, c, g, or t

<400> SEQUENCE: 5
gtattgtcnt ncnnatcctc gnnctngctg tcnt                                34

<210> SEQ ID NO 6
<211> LENGTH: 14
<212> TYPE: DNA
<213> ORGANISM: Artificial
<220> FEATURE:
<223> OTHER INFORMATION: bisphenol A aptamer

<400> SEQUENCE: 6
gcgggtaccg tgct                                                      14

<210> SEQ ID NO 7
<211> LENGTH: 22
<212> TYPE: DNA
<213> ORGANISM: Artificial
<220> FEATURE:
<223> OTHER INFORMATION: bisphenol A aptamer
<220> FEATURE:
<221> NAME/KEY: misc_feature
<222> LOCATION: (11)..(12)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (21)..(21)
<223> OTHER INFORMATION: n is a, c, g, or t

<400> SEQUENCE: 7
cggtgggtgg nnagntgnga na                                             22
```

```
<210> SEQ ID NO 8
<211> LENGTH: 60
<212> TYPE: DNA
<213> ORGANISM: Artificial
<220> FEATURE:
<223> OTHER INFORMATION: bisphenol A aptamer

<400> SEQUENCE: 8
cggccctagg atgacctgag tactgtccct caccectact tccgccactg gcccaacagc      60

<210> SEQ ID NO 9
<211> LENGTH: 60
<212> TYPE: DNA
<213> ORGANISM: Artificial
<220> FEATURE:
<223> OTHER INFORMATION: bisphenol A aptamer

<400> SEQUENCE: 9
tgcctaggat gacctgagta ctgtccaggc tccgaccttg tccctgccgc cactctccca      60

<210> SEQ ID NO 10
<211> LENGTH: 60
<212> TYPE: DNA
<213> ORGANISM: Artificial
<220> FEATURE:
<223> OTHER INFORMATION: bisphenol A aptamer

<400> SEQUENCE: 10
gcggacgggc tcggctcacc taggatgacc tgagtactgt ccccgtggcg ctaattcggg      60

<210> SEQ ID NO 11
<211> LENGTH: 60
<212> TYPE: DNA
<213> ORGANISM: Artificial
<220> FEATURE:
<223> OTHER INFORMATION: bisphenol A aptamer

<400> SEQUENCE: 11
cggcccgccc ctaggatgac ctgagtactg tccgcgggac ggtatcgctg agacaggtgc      60

<210> SEQ ID NO 12
<211> LENGTH: 60
<212> TYPE: DNA
<213> ORGANISM: Artificial
<220> FEATURE:
<223> OTHER INFORMATION: bisphenol A aptamer

<400> SEQUENCE: 12
cggcagccct aggatgacct gagtactgtc cgcgaaagac tccatggtac ccggtgctta      60

<210> SEQ ID NO 13
<211> LENGTH: 58
<212> TYPE: DNA
<213> ORGANISM: Artificial
<220> FEATURE:
<223> OTHER INFORMATION: bisphenol A aptamer
<220> FEATURE:
<221> NAME/KEY: misc_feature
<222> LOCATION: (11)..(11)
<223> OTHER INFORMATION: n is a, c, g, or t
<220> FEATURE:
<221> NAME/KEY: misc_feature
<222> LOCATION: (40)..(40)
<223> OTHER INFORMATION: n is a, c, g, or t

<400> SEQUENCE: 13
gggggcgtcg ncctaggatg acctgagtac tgtccgcacn cagggaggat gcattgac       58
```

```
<210> SEQ ID NO 14
<211> LENGTH: 60
<212> TYPE: DNA
<213> ORGANISM: Artificial
<220> FEATURE:
<223> OTHER INFORMATION: bisphenol A aptamer

<400> SEQUENCE: 14
gtgtccccac gtcctaggat gacctgagta ctgtccaatg ccgctcctcc cgatgcagac     60

<210> SEQ ID NO 15
<211> LENGTH: 60
<212> TYPE: DNA
<213> ORGANISM: Artificial
<220> FEATURE:
<223> OTHER INFORMATION: bisphenol A aptamer
<220> FEATURE:
<221> NAME/KEY: misc_feature
<222> LOCATION: (7)..(7)
<223> OTHER INFORMATION: n is a, c, g, or t

<400> SEQUENCE: 15
ctcttcnctc caattcgtaa gatgacctga ggtctgccca acggtgttta gaacccttg      60

<210> SEQ ID NO 16
<211> LENGTH: 60
<212> TYPE: DNA
<213> ORGANISM: Artificial
<220> FEATURE:
<223> OTHER INFORMATION: bisphenol A aptamer

<400> SEQUENCE: 16
cgcagcgcgc ccctgagtac tgtccgccca acggtgtgac ggccctgcga tcaacgattg     60

<210> SEQ ID NO 17
<211> LENGTH: 60
<212> TYPE: DNA
<213> ORGANISM: Artificial
<220> FEATURE:
<223> OTHER INFORMATION: bisphenol A aptamer

<400> SEQUENCE: 17
gggccgtcct aggatgacct gagtactgtc cgcccaacgg tgtgacggcc ctgcgatcaa     60

<210> SEQ ID NO 18
<211> LENGTH: 60
<212> TYPE: DNA
<213> ORGANISM: Artificial
<220> FEATURE:
<223> OTHER INFORMATION: bisphenol A aptamer

<400> SEQUENCE: 18
ccctcgccct gagtactgtc ccccgtccgt ccggtgaggg ccactatcgc taactgatca     60

<210> SEQ ID NO 19
<211> LENGTH: 60
<212> TYPE: DNA
<213> ORGANISM: Artificial
<220> FEATURE:
<223> OTHER INFORMATION: bisphenol A aptamer

<400> SEQUENCE: 19
aggccgttgg tgtggtgggc ctagggccgg cggcgcacag ctgttataga cgtctccagc     60

<210> SEQ ID NO 20
<211> LENGTH: 60
<212> TYPE: DNA
```

```
<213> ORGANISM: Artificial
<220> FEATURE:
<223> OTHER INFORMATION: bisphenol A aptamer

<400> SEQUENCE: 20
ccgccgttgg tgtggtgggc ctagggccgg cggcgcacag ctgttataga cgtctccagc    60

<210> SEQ ID NO 21
<211> LENGTH: 60
<212> TYPE: DNA
<213> ORGANISM: Artificial
<220> FEATURE:
<223> OTHER INFORMATION: bisphenol A aptamer

<400> SEQUENCE: 21
ccgccgttgg tgtggtgggc ctagggccgg cggcgcacag ctgttataga cgcctccagc    60

<210> SEQ ID NO 22
<211> LENGTH: 60
<212> TYPE: DNA
<213> ORGANISM: Artificial
<220> FEATURE:
<223> OTHER INFORMATION: bisphenol A aptamer

<400> SEQUENCE: 22
ccgccgttgg tgtggtgggc ccagggccgg cggcgcacag ctgttataga cgcctccagc    60

<210> SEQ ID NO 23
<211> LENGTH: 60
<212> TYPE: DNA
<213> ORGANISM: Artificial
<220> FEATURE:
<223> OTHER INFORMATION: bisphenol A aptamer

<400> SEQUENCE: 23
tgacggtggc gtggagggcg cgtatcaatc gttgatcgca gggccgtcat accgttggag    60

<210> SEQ ID NO 24
<211> LENGTH: 61
<212> TYPE: DNA
<213> ORGANISM: Artificial
<220> FEATURE:
<223> OTHER INFORMATION: bisphenol A aptamer

<400> SEQUENCE: 24
tgacggtggc gtggagggcg cgtatcaatc gttgatcgca gggccgtcat accgttgggg    60
g                                                                   61

<210> SEQ ID NO 25
<211> LENGTH: 60
<212> TYPE: DNA
<213> ORGANISM: Artificial
<220> FEATURE:
<223> OTHER INFORMATION: bisphenol A aptamer

<400> SEQUENCE: 25
tgacggtggc gtggagggcg cgtatcaatc gttgatcgca gggccgtcat accggtcggg    60

<210> SEQ ID NO 26
<211> LENGTH: 60
<212> TYPE: DNA
<213> ORGANISM: Artificial
<220> FEATURE:
<223> OTHER INFORMATION: bisphenol A aptamer

<400> SEQUENCE: 26
```

```
gccgacaggg catgggacgc tatcagcggt gtcaatcgaa ttcccgcggc cgccatgcgg      60
```

<210> SEQ ID NO 27
<211> LENGTH: 60
<212> TYPE: DNA
<213> ORGANISM: Artificial
<220> FEATURE:
<223> OTHER INFORMATION: bisphenol A aptamer

<400> SEQUENCE: 27

```
ggtccccgca gctcatacgg cgctccagcg taatcgaatt cccgcggccg ccatgcggcc      60
```

<210> SEQ ID NO 28
<211> LENGTH: 60
<212> TYPE: DNA
<213> ORGANISM: Artificial
<220> FEATURE:
<223> OTHER INFORMATION: bisphenol A aptamer

<400> SEQUENCE: 28

```
gcgagtggcc catcagcaga gcgtaatccc cacgcacatc gagtgccccc ggccggtgct      60
```

<210> SEQ ID NO 29
<211> LENGTH: 57
<212> TYPE: DNA
<213> ORGANISM: Artificial
<220> FEATURE:
<223> OTHER INFORMATION: bisphenol A aptamer

<400> SEQUENCE: 29

```
gtattgtcat tcatatcctc gtgcttgctg tcctcacccc acccaccaga atggaaa         57
```

<210> SEQ ID NO 30
<211> LENGTH: 60
<212> TYPE: DNA
<213> ORGANISM: Artificial
<220> FEATURE:
<223> OTHER INFORMATION: bisphenol A aptamer

<400> SEQUENCE: 30

```
cctggtattg tcttgccaat cctcgccctg gctgtcttac ccctccccac ccgcctgaag      60
```

<210> SEQ ID NO 31
<211> LENGTH: 63
<212> TYPE: DNA
<213> ORGANISM: Artificial
<220> FEATURE:
<223> OTHER INFORMATION: bisphenol A aptamer

<400> SEQUENCE: 31

```
gtcgactcgc gggtaccgtg ctcaatgtcc caatccgggg aagcgtttag acccgcagcc      60
cac                                                                    63
```

<210> SEQ ID NO 32
<211> LENGTH: 58
<212> TYPE: DNA
<213> ORGANISM: Artificial
<220> FEATURE:
<223> OTHER INFORMATION: bisphenol A aptamer
<220> FEATURE:
<221> NAME/KEY: misc_feature
<222> LOCATION: (29)..(29)
<223> OTHER INFORMATION: n is a, c, g, or t
<220> FEATURE:
<221> NAME/KEY: misc_feature
<222> LOCATION: (37)..(37)
<223> OTHER INFORMATION: n is a, c, g, or t
<220> FEATURE:

```
<221> NAME/KEY: misc_feature
<222> LOCATION: (41)..(41)
<223> OTHER INFORMATION: n is a, c, g, or t
<220> FEATURE:
<221> NAME/KEY: misc_feature
<222> LOCATION: (44)..(45)
<223> OTHER INFORMATION: n is a, c, g, or t
<220> FEATURE:
<221> NAME/KEY: misc_feature
<222> LOCATION: (55)..(55)
<223> OTHER INFORMATION: n is a, c, g, or t

<400> SEQUENCE: 32
gtcgccactg cgggtaccgt gcttgggcna ccgatgnacc ntgnnaccgt gtttngcc        58

<210> SEQ ID NO 33
<211> LENGTH: 63
<212> TYPE: DNA
<213> ORGANISM: Artificial
<220> FEATURE:
<223> OTHER INFORMATION: bisphenol A aptamer

<400> SEQUENCE: 33
ccggtgggtg gtcaggtggg atagcgttcc gcgtatggcc cagcgcatca cgggttcgca     60
cca                                                                    63

<210> SEQ ID NO 34
<211> LENGTH: 60
<212> TYPE: DNA
<213> ORGANISM: Artificial
<220> FEATURE:
<223> OTHER INFORMATION: bisphenol A aptamer

<400> SEQUENCE: 34
gggcggtggg tggcgagttg tgagacgctg gaggaggttg ctgccccgg cacattggga      60

<210> SEQ ID NO 35
<211> LENGTH: 106
<212> TYPE: DNA
<213> ORGANISM: Artificial
<220> FEATURE:
<223> OTHER INFORMATION: random ssDNA library
<220> FEATURE:
<221> NAME/KEY: misc_feature
<222> LOCATION: (23)..(82)
<223> OTHER INFORMATION: n is a, c, g, or t

<400> SEQUENCE: 35
gggccgttcg aacacgagca tgnnnnnnnn nnnnnnnnnn nnnnnnnnnn nnnnnnnnnn     60
nnnnnnnnnn nnnnnnnnnn nnggacagta ctcaggtcat cctagg                   106

<210> SEQ ID NO 36
<211> LENGTH: 22
<212> TYPE: DNA
<213> ORGANISM: Artificial
<220> FEATURE:
<223> OTHER INFORMATION: forward primer

<400> SEQUENCE: 36
gggccgttcg aacacgagca tg                                              22

<210> SEQ ID NO 37
<211> LENGTH: 24
<212> TYPE: DNA
<213> ORGANISM: Artificial
<220> FEATURE:
<223> OTHER INFORMATION: reverse primer
```

```
<400> SEQUENCE: 37
cctaggatga cctgagtact gtcc                                          24

<210> SEQ ID NO 38
<211> LENGTH: 44
<212> TYPE: DNA
<213> ORGANISM: Artificial
<220> FEATURE:
<223> OTHER INFORMATION: bisphenol A trimmed form aptamer

<400> SEQUENCE: 38
cggtgggtgg tcaggtggga tagcgttccg cgtatggccc agcg                    44

<210> SEQ ID NO 39
<211> LENGTH: 49
<212> TYPE: DNA
<213> ORGANISM: Artificial
<220> FEATURE:
<223> OTHER INFORMATION: bisphenol A trimmed form aptamer

<400> SEQUENCE: 39
tgccggtggg tggtcaggtg ggatagcgtt ccgcgtatgg cccagcgca               49

<210> SEQ ID NO 40
<211> LENGTH: 56
<212> TYPE: DNA
<213> ORGANISM: Artificial
<220> FEATURE:
<223> OTHER INFORMATION: bisphenol A trimmed form aptamer

<400> SEQUENCE: 40
agcatgccgg tgggtggtca ggtgggatag cgttccgcgt atggcccagc gcatca       56

<210> SEQ ID NO 41
<211> LENGTH: 66
<212> TYPE: DNA
<213> ORGANISM: Artificial
<220> FEATURE:
<223> OTHER INFORMATION: bisphenol A trimmed form aptamer

<400> SEQUENCE: 41
acacgagcat gccggtgggt ggtcaggtgg gatagcgttc cgcgtatggc ccagcgcatc   60
acgggt                                                              66
```

NUCLEIC ACID APTAMER WHICH SPECIFICALLY BINDS TO BISPHENOL A

TECHNICAL FIELD

The present invention relates to a nucleic acid aptamer capable of binding specifically to bisphenol A and a method of detecting and removing bisphenol A using the same.

BACKGROUND ART

Bisphenol A, a raw material for preparing plastics such as polycarbonate or epoxy resins, is widely used in the manufacture of nursing bottles, dental resins, coatings for beverage cans, etc. However, bisphenol A is an endocrine disrupter (environmental hormone) which can act as a synthetic estrogen. When it is absorbed into an organism, it interferes with or disturbs the normal function of the endocrine system. Even when it exists in an organism in a very small amount, it will cause serious disorders, including reproductive dysfunction, growth retardation, malformation and cancer, by biosorption. For this reason, detection of bisphenol A in natural systems is essential for public health and environmental protection.

In the examination of trace hazardous materials in the environmental and food industries, the evaluation of safety in the pharmaceutical industry, etc., detection of environmental hormones such as bisphenol A has been requested, but there has been significant difficulty in detecting a trace amount of bisphenol A. Thus, there has been a need to develop a novel technology capable of effectively detecting and removing bisphenol A.

Meanwhile, aptamers which are single-stranded DNA or RNA molecules refer to small single-stranded oligonucleotides that can bind specifically to their target with high affinity. Aptamers have been recognized as substitutes for antibodies, because these aptamers can be used as components for biosensors capable of recognizing molecules in detection/analysis systems. Particularly, unlike antibodies, aptamers can be used as molecules targeting various organic and inorganic substances, including toxin, and once an aptamer binding specifically to a certain substance is isolated, it can be consistently produced at low costs using automated oligomer synthesis methods. Since an aptamer-based biosensor of detecting a target protein using a fluorescence-labeled aptamer was first developed in 1996, various biosensors based on the advantages and structural characteristics of aptamers have been developed (Yeon-Seok KIM & Man-Bock GU, NICE, 26(6): 690, 2008), and discovery of new aptamers capable of detecting various chemical substances has been requested.

Accordingly, the present inventors have made many efforts to isolate an aptamer that binds specifically to bisphenol so as to be capable of effectively detecting and removing bisphenol. As a result, the present inventors have selected an aptamer binding specifically only to bisphenol A using the SELEX (Systematic Evolution of Ligands by EXponential enrichment) process and have found that the selected aptamer binds specifically only to bisphenol A without binding to other bisphenols, including bisphenol B, which have structures similar thereto, thereby completing the present invention.

DISCLOSURE OF INVENTION

It is an object of the present invention to provide an aptamer binding specifically only to bisphenol A.

Another object of the present invention is to provide a composition, kit and sensor for detecting bisphenol A, which contains said aptamer.

Still another object of the present invention is to provide a method of detecting and removing bisphenol A using said aptamer.

To achieve the above objects, the present invention provides a nucleic acid aptamer capable of binding specifically to bisphenol A, which comprises any one of nucleic acid sequences set forth in SEQ ID NO: 1 to SEQ ID NO: 7.

The present invention also provides a nucleic acid aptamer capable of binding specifically to bisphenol A, which is a nucleic acid sequence having a homology of at least 90%, but less than 100%, with any one of nucleic acid sequences set forth in SEQ ID NO: 8 to SEQ ID NO: 34.

The present invention also provides a method of detecting or removing bisphenol A using said aptamer.

The present invention also provides a composition for detecting or removing bisphenol A, which contains said aptamer.

The present invention also provides a kit and sensor for detecting bisphenol, which contains said aptamer.

The present invention also provides the use of a nucleic acid aptamer, which can bind specifically to bisphenol A, for detecting or removing bisphenol A, wherein the nucleic acid aptamer comprises any one of nucleic acid sequences set forth in SEQ ID NO: 1 to SEQ ID NO: 7.

Other features and embodiments of the present invention will be more apparent from the following detailed descriptions and the appended claims.

BEST MODE FOR CARRYING OUT THE INVENTION

Figure 1:
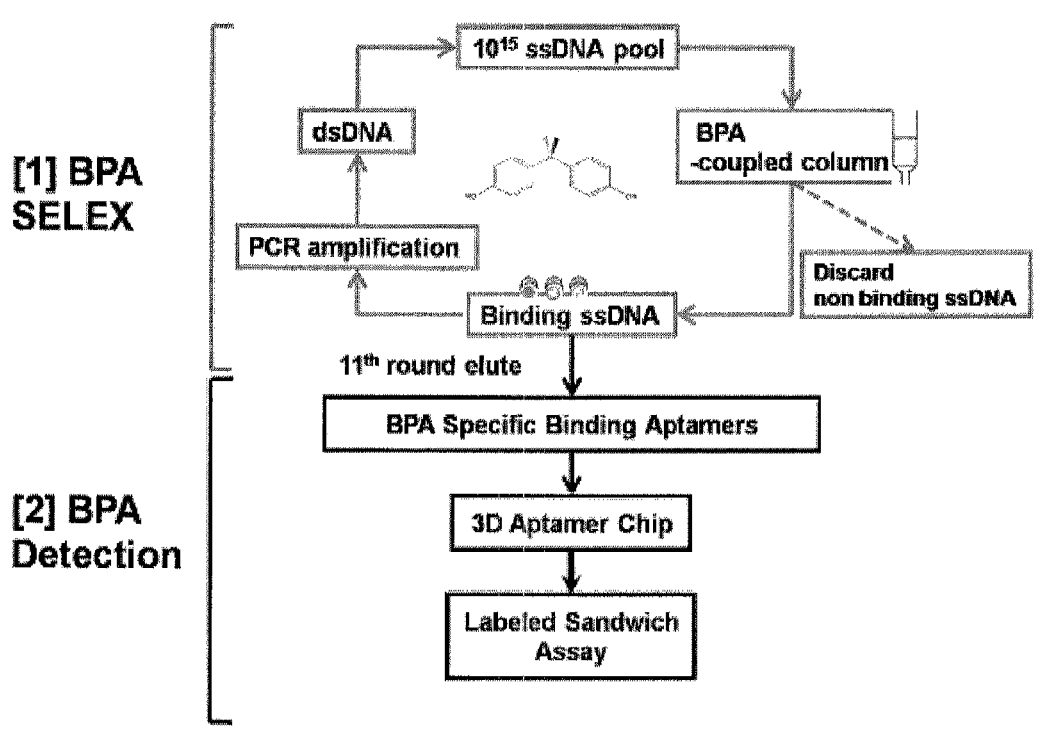
FIG. 1 is a schematic view showing a process of selecting an aptamer binding specifically to bisphenol A according to the present invention and a process of detecting bisphenol A.

Unless defined otherwise, all technical and scientific terms used herein have the same meaning as commonly understood by one of ordinary skill in the art to which the invention pertains. Generally, the nomenclature used herein and the experiment methods are those well known and commonly employed in the art.

The definition of main terms used in the detailed description of the invention is as follows.

As used herein, the term "aptamer" refers to a small single-stranded oligonucleotide that can bind specifically to its target with high affinity. If the aptamer is RNA, T in the specified nucleic acid sequence is preferably U.

As used herein, the term "sample" refers to a composition that might contain an analyte of interest to be analyzed.

As used herein, the phrase "nucleic acid sequence having a homology of at least 90%, but less than 100%" refers to a nucleic acid sequence which comprises an addition, deletion or substitution of one to several nucleotides relative to a reference sequence to have a sequence homology of at least 90%, but less than 100%, with the reference sequence, and to show a bisphenol A-binding affinity similar to the reference sequence.

In one aspect, the present invention is directed to a nucleic acid aptamer capable of binding specifically to bisphenol A, which comprises any one of nucleic acid sequences set forth in SEQ ID NO: 1 to SEQ ID NO: 7.

```
SEQ ID NO: 1:
5'-CCTGAGKWAC TGYCC-3'
(K = G or T, W = A or T, Y = T or C)

SEQ ID NO: 2:
5'-GCCGTTGGTG TGGTGGGCCY AGGGCCGGCG GCGCACAGCT

GTTATAGACG YCTCCAGC-3'
(Y = C or T)

SEQ ID NO: 3:
5'-TGACGGTGGC GTGGAGGGCG CGTATCAATC GTTGATCGCA

GGGCCGTCAT ACCGKTSGRG-3'
(K = G or T, S = C or G, R = A or G)

SEQ ID NO: 4:
5'-ATCGARTKCC CSCGGCCG-3'
(R = A or G; K = G or T; S = C or G)

SEQ ID NO: 5:
5'-GTATTGTCNT NCNNATCCTC GNNCTNGCTG TCNT-3'
(N = A, T, C or G)

SEQ ID NO: 6:
5'-GCGGGTACCG TGCT-3'

SEQ ID NO: 7:
5'-CGGTGGGTGG NNAGNTGNGA NA-3'
(N = A, T, C or G)
```

In this regard, the total number of nucleotides in the aptamer may be 14-200 nts, and preferably 14-63 nts.

In the present invention, the nucleic acid aptamer comprising the nucleic acid sequence of SEQ ID NO: 1 may be any one of nucleic acid sequences set forth in SEQ ID NO: 8 to SEQ ID NO: 18.

```
#31:
                                        (SEQ ID NO: 8)
5'-CGGCCCTAGG ATGACCTGAG TACTGTCCCT CACCCCTACT

TCCGCCACTG GCCCAACAGC-3'

#23:
                                        (SEQ ID NO: 9)
5'-TGCCTAGGAT GACCTGAGTA CTGTCCAGGC TCCGACCTTG

TCCCTGCCGC CACTCTCCCA-3'

#47:
                                        (SEQ ID NO: 10)
5'-GCGGACGGGC TCGGCTCACC TAGGATGACC TGAGTACTGT

CCCCGTGGCG CTAATTCGGG-3'

#50:
                                        (SEQ ID NO: 11)
5'-CGGCCCGCCC CTAGGATGAC CTGAGTACTG TCCGCGGGAC

GGTATCGCTG AGACAGGTGC-3'

#41:
                                        (SEQ ID NO: 12)
5'-CGGCAGCCCT AGGATGACCT GAGTACTGTC CGCGAAAGAC

TCCATGGTAC CCGGTGCTTA-3'

#27:
                                        (SEQ ID NO: 13)
5'-GGGGGCGTCG NCCTAGGATG ACCTGAGTAC TGTCCGCACN

CAGGGAGGAT GCATTGAC-3'

#45:
                                        (SEQ ID NO: 14)
5'-GTGTCCCCAC GTCCTAGGAT GACCTGAGTA CTGTCCAATG

CCGCTCCTCC CGATGCAGAC-3'

#11:
                                        (SEQ ID NO: 15)
5'-CTCTTCNCTC CAATTCGTAA GATGACCTGA GGTCTGCCCA

ACGGTGTTTA GAACCCCTTG-3'

#12-3:
                                        (SEQ ID NO: 16)
5'-CGCAGCGCGC CCCTGAGTAC TGTCCGCCCA ACGGTGTGAC

GGCCCTGCGA TCAACGATTG-3'

#12-4:
                                        (SEQ ID NO: 17)
5'-GGGCCGTCCT AGGATGACCT GAGTACTGTC CGCCCAACGG

TGTGACGGCC CTGCGATCAA-3'

#22:
                                        (SEQ ID NO: 18)
5'-CCCTCGCCCT GAGTACTGTC CCCCGTCCGT CCGGTGAGGG

CCACTATCGC TAACTGATCA-3'
```

In the present invention, the nucleic acid aptamer comprising the nucleic acid sequence of SEQ ID NO: 2 may be any one of nucleic acid sequences set forth in SEQ ID NO: 19 to SEQ ID NO: 22.

```
#4:
                                        (SEQ ID NO: 19)
5'-AGGCCGTTGG TGTGGTGGGC CTAGGGCCGG CGGCGCACAG

CTGTTATAGA CGTCTCCAGC-3'

#12-5:
                                        (SEQ ID NO: 20)
5'-CCGCCGTTGG TGTGGTGGGC CTAGGGCCGG CGGCGCACAG

CTGTTATAGA CGTCTCCAGC-3'

#6:
                                        (SEQ ID NO: 21)
5'-CCGCCGTTGG TGTGGTGGGC CTAGGGCCGG CGGCGCACAG

CTGTTATAGA CGCCTCCAGC-3'
```

12-7:
(SEQ ID NO: 22)
5'-CC<u>GCCGTTGG TGTGGTGGGC CCAGGGCCGG CGGCGCACAG</u>

<u>CTGTTATAGA CGCCTCCAGC</u>-3'

In the present invention, the nucleic acid aptamer comprising the nucleic acid sequence of SEQ ID NO: 3 may be any one of nucleic acid sequences set forth in SEQ ID NO: 23 to SEQ ID NO: 25.

12-2:
(SEQ ID NO: 23)
5'-<u>TGACGGTGGC GTGGAGGGCG CGTATCAATC GTTGATCGCA</u>

<u>GGGCCGTCAT ACCGTTGGAG</u>-3'

12-9:
(SEQ ID NO: 24)
5'-<u>TGACGGTGGC GTGGAGGGCG CGTATCAATC GTTGATCGCA</u>

<u>GGGCCGTCAT ACCGTTGGGG</u>-3'

12-6:
(SEQ ID NO: 25)
5'-<u>TGACGGTGGC GTGGAGGGCG CGTATCAATC GTTGATCGCA</u>

<u>GGGCCGTCAT ACCGGTCGGG</u>-3'

In the present invention, the nucleic acid aptamer comprising the nucleic acid sequence of SEQ ID NO: 4 may be any one of nucleic acid sequences set forth in SEQ ID NO: 26 to SEQ ID NO: 28.

2:
(SEQ ID NO: 26)
5'-GCCGACAGGG CATGGGACGC TATCAGCGGT GTC<u>AATCGAA</u>

<u>TTCCCGCGGC CGCCATGCGG</u>-3'

14:
(SEQ ID NO: 27)
5'-GGTCCCCGCA GCTCATACGG CGCTCCAGCG <u>TAATCGAATT</u>

<u>CCCGCGGCCG</u> CCATGCGGCC-3'

46:
(SEQ ID NO: 28)
5'-GCGAGTGGCC CATCAGCAGA GCGTAATCCC CACGCAC<u>ATC</u>

<u>GAGTGCCCCC GGCCGG</u>TGCT-3'

In the present invention, the nucleic acid aptamer comprising the nucleic acid sequence of SEQ ID NO: 5 may be a nucleic acid sequence set forth in SEQ ID NO: 29 or SEQ ID NO: 30.

12:
(SEQ ID NO: 29)
5'-<u>GTATTGTCAT TCATATCCTC GTGCTTGCTG TCCTCACCCC</u>

<u>ACCCACCAGA ATGGAAA</u>-3'

13:
(SEQ ID NO: 30)
5'-CCTGG<u>TATTG TCTTGCCAAT CCTCGCCCTG GCTGTCTTAC</u>

CCCTCCCCAC CGCCTGAAG-3'

In the present invention, the nucleic acid aptamer comprising the nucleic acid sequence of SEQ ID NO: 6 may be a nucleic acid sequence set forth in SEQ ID NO: 31 or SEQ ID NO: 32.

48:
(SEQ ID NO: 31)
5'-<u>GTCGACTC</u>GC <u>GGGTACCGTG CT</u>CAATGTCC CAATCCGGGG

AAGCGTTTAG ACCCGCAGCC CAC-3'

40:
(SEQ ID NO: 32)
5'-<u>GTCGCC</u>ACT<u>G CGGGTACCGT GCT</u>TGGGCNA CCGATGNACC

NTGNNACCGT GTTTNGCC-3'

In the present invention, the nucleic acid aptamer comprising the nucleic acid sequence of SEQ ID NO: 6 may be a nucleic acid sequence set forth in SEQ ID NO: 33 or SEQ ID NO: 34.

3:
(SEQ ID NO: 33)
5'-C<u>CGGTGGGTG GTCAGGTGGG ATA</u>GCGTTCC GCGTATGGCC

CAGCGCATCA CGGGTTCGCA CCA-3'

32:
(SEQ ID NO: 34)
5'-GGG<u>CGGTGGG TGGCGAGTTG TGAGA</u>CGCTG GAGGAGGTTG

CTGCCCCCGG CACATTGGGA-3'

The nucleic acid aptamer is provided in the form of a single-stranded DNA or RNA molecule. In the present invention, if the nucleic acid is RNA, "T" in the nucleic acid sequence is to be read as "U", and it will be obvious to a person of ordinary skill in the art that this sequence falls within the scope of the present invention.

In one Example of the present invention, as shown in FIG. 1, the aptamers having the nucleic acid sequences set forth in SEQ ID NOS: 8 to 34 were selected through the SELEX process, and then the affinities of the selected aptamers for bisphenol A were measured using a real-time PCR assay and an equilibrium filtration method. As a result, it was found that the nucleic acid sequences set forth in SEQ ID NOS: 8 to 34 did bind specifically to bisphenol A. The bisphenol A-specific aptamers that are the nucleic acid sequences set forth in SEQ ID NOS: 8 to 34 have commonly conserved regions as shown in SEQ ID NOS: 1 to 7, and thus aptamers having such commonly conserved regions can bind specifically to bisphenol A. The presence of such commonly conserved regions means that a nucleic acid sequence having a homology of at least 90%, but less than 100%, with any one selected from among the nucleic acid sequences set forth in SEQ ID NO: 8 to SEQ ID NO: 34, is a nucleic acid aptamer that can bind specifically to bisphenol A. In the case of group 1, eleven aptamers having the consensus sequence of SEQ ID NO: 1 were obtained and these aptamers all did bind specifically to bisphenol A, suggesting that a nucleic acid sequence having a homology of 90% or more with these aptamers can also bind specifically to bisphenol A.

In another Example of the present invention, aptamer #3 (nucleic acid sequence set forth in SEQ ID NO: 33), which showed the highest affinity among the nucleic acid aptamers set forth in SEQ ID NOS: 8 to 34, was measured for its affinities (Kd) for bisphenols other than bisphenol A, for example, bisphenol B (BPB), 4,4'-bisphenol (BP), 6F bisphenol A (6F) and the like, according to the method of Example 2-2. As a result, aptamer #3 did not show affinity for BPB and showed specific affinity only for bisphenol A, even though BPB has no difference from bisphenol A except for a single methyl group.

In another aspect, the present invention relates to a method of detecting bisphenol A using the aptamer of the present invention. In this regard, bisphenol A is preferably detected in a sample taken from any one of, but not limited to, water, soil, air, food, waste, animal and plant organs, and animal and plant tissues. Herein, examples of the water include river water, seawater, lake water and rainwater, and the animals and plants include the human body.

In another Example of the present invention, aptamer #3 (nucleic acid sequence set forth in SEQ ID NO: 33), which showed the highest affinity among the nucleic acid aptamers set forth in SEQ ID NOS: 8 to 34, was analyzed for its affinity for bisphenol A by a sandwich assay using a sol-gel chip. As a result, it was shown that aptamer #3 did bind specifically to bisphenol A. Accordingly, the present invention relates to a sensor for detecting bisphenol A, which contains an aptamer binding specifically to bisphenol A.

The detection sensor system of the present invention may take the form of bottles, tubs, sachets, envelops, tubes, ampoules, and the like, which may be formed in part or in whole from plastic, glass, paper, foil, wax, and the like. The sensor container may be equipped with a fully or partially detachable lid that may initially be part of the container or may be affixed to the container by mechanical, adhesive, or other means. The container may also be equipped with a stopper, allowing access to the contents by a syringe needle. The detection kit may comprise an exterior package which may include instructions regarding the use of the components.

The inventive aptamer binding specifically to bisphenol A can specifically detect only bisphenol A, and thus it will be obvious to a person of ordinary skill in the art that a composition for detecting or removing bisphenol A comprising the aptamer of the present invention can be provided.

In still another aspect, the present invention relates to a method of removing bisphenol A using an aptamer binding specifically to bisphenol A. According to one preferred embodiment of the present invention, bisphenol A can be removed by packing beads having the aptamer fixed thereto into a column and passing a bisphenol A-containing sample through the column.

EXAMPLES

Hereinafter, the present invention will be described in further detail with reference to examples. It will be obvious to a person having ordinary skill in the art that these examples are illustrative purposes only and are not to be construed to limit the scope of the present invention.

Example 1

Isolation of Aptamers Binding Specifically to Bisphenol A 1-1: Preparation of Bisphenol A-Agarose Affinity Column In order to isolate aptamers binding specifically to bisphenol A, a bisphenol A-agarose affinity column was prepared in the following manner.

First, 20 mM bisphenol A (4,4'-dihydroxy-2,2-diphenylpropane, Sigma-Aldrich, USA) was dissolved in 50% DMF. Epoxy-activated Sepharose 6B resin (GE Healthcare Bio-Sciences Corp., USA) was used to immobilize bisphenol A via ether linkages to hydroxyl groups. Bisphenol A was coupled overnight with 600 µl of the epoxy-activated resin (having about 11-24 µmole of active groups) in coupling buffer (50% DMF, pH 13.0) at 38° C. with shaking at 5 rpm.

The target-coupled resin was washed sequentially with coupling buffer, 1 M acetate buffer and distilled water, after which the coupled resin was incubated with 1 M ethanolamine (pH 8.0) with shaking at 42° C. for 6 hours, thereby blocking the free/unoccupied groups formed during the immobilization process. After the blocking process, the beads were washed with washing buffer (0.1 M acetate, 0.5 M NaCl, pH 4.0), re-suspended in 20% ethanol, and then stored at 4° C. until use.

The amount of unbound bisphenol A in the washing buffer, which was discarded, was measured using a spectrometer (Bio-Rad, USA) at 280 nm, and the concentration of bisphenol A bound to the resin was calculated based on the difference between the initial concentration of bisphenol A and the concentration of unbound bisphenol A. As a control, resin blocked with ethanolamine without being coupled with bisphenol A was used.

1-2: Preparation of ssDNA Pool and Selection of Aptamers Binding Specifically to Bisphenol A A random ssDNA library having the following sequence was chemically synthesized and purified by PAGE (Genotech Inc., Korea):

(SEQ ID NO: 35)
5'-GGGCCGTTCGAACACGAGCATG-$N_{60}$-GGACAGTACTCAGGTCATCC

TAGG-3'

An asymmetric PCR process was performed to prepare ssDNA, and the concentration of ssDNA was measured using Quant-iT Oligreen ssDNA reagent and kit (Invitrogen, USA). ssDNA was confirmed using nuclease S1 (Sigma-Aldrich, USA). The initial pool included $10^{15}$ molecule. In the asymmetric PCR, only the following forward primer was used:

Forward primer:
(SEQ ID NO: 36)
5'-GGGCCGTTCGAACACGAGCATG-3'

The SELEX process for aptamer selection and amplification was performed 12 times. Specifically, the bisphenol A-coupled resin was washed with binding buffer (25 mM Tris-HCl, 100 mM NaCl, 25 mM KCl, 10 mM $MgCl_2$, 5% DMSO, pH 8) before each SELEX round. The random ssDNA library pool was heated at 95° C. for 5 minutes and then cooled to room temperature for 1-2 hours. In every selection round, 19 µmole of bisphenol A coupled to 600 µl of resin was mixed with random DNA pool in binding buffer. The mixture was incubated in a yellow column (Bio-Rad, USA) at room temperature for 1 hour. Unbound ssDNA was removed by washing the resin with binding buffer.

To elute bound ssDNA from the bisphenol A-coupled resin, elution buffer (50 mM Bisphenol A, 100 mM Tris-HCl, 200 mM NaCl, 25 mM KCl, 10 mM MgCl2, 50% DMSO, pH 8.0) was added to the column, and the eluent was collected. To precipitate the eluted ssDNA, 20 µg of yeast tRNA was added as a carrier. After round 3, a negative selection step was performed to remove unbound candidates from the resin. After selection rounds 9 and 11, the eluted aptamer pools were cloned with a pGEMT easy vector system (Promega, USA), and each clone was sequenced (Solgent Inc., Korea).

From rounds 11 and 12, 54 aptamers were selected, but some of these selected aptamers were shown to overlap each other. As a result, as shown below, a total of 27 aptamers were selected:

Group 1
31
(SEQ ID NO: 8)
5'-CGGCCCTAGG ATGA<u>CCTGAG TACTGTCC</u>CT CACCCCTACT TCCGCCACTG GCCCAACAGC-3'

23
(SEQ ID NO: 9)
5'-TGCCTAGGAT GA<u>CCTGAGTA CTGTCC</u>AGGC TCCGACCTTG TCCCTGCCGC CACTCTCCCA-3'

47
(SEQ ID NO: 10)
5'-GCGGACGGGC TCGGCTCACC TAGGATGA<u>CC TGAGTACTGT CC</u>CCGTGGCG CTAATTCGGG-3'

50
(SEQ ID NO: 11)
5'-CGGCCCGCCC CTAGGATGA<u>C CTGAGTACTG TCCGC</u>GGGAC GGTATCGCTG AGACAGGTGC-3'

41
(SEQ ID NO: 12)
5'-CGGCAGC<u>CCT</u> AGGATGA<u>CCT GAGTACTGTC CGC</u>GAAAGAC TCCATGGTAC CCGGTGCTTA-3'

27
(SEQ ID NO: 13)
5'-GGGGGCGTCG NCCTAGGATG A<u>CCTGAGTAC TGTCCGC</u>ACN CAGGGAGGAT GCATTGAC-3'

45
(SEQ ID NO: 14)
5'-GTGTCCCCAC GTCCTAGGAT GA<u>CCTGAGTA CTGTCC</u>AATG CCGCTCCTCC CGATGCAGAC-3'

11
(SEQ ID NO: 15)
5'-CTCTTCNCTC CAATTCGTAA GATGA<u>CCTGA G</u>GT<u>CTGCCC</u>A ACGGTGTTTA GAACCCCTTG-3'

12-3
(SEQ ID NO: 16)
5'-CGCAGCGCGC C<u>CCTGAGTAC TGTCCGC</u>CCA ACGGTGTGAC GGCCCTGCGA TCAACGATTG-3'

12-4
(SEQ ID NO: 17)
5'-GGGCCGTCCT AGGATGA<u>CCT GAGTACTGTC CGC</u>CCAACGG TGTGACGGCC CTGCGATCAA-3'

22
(SEQ ID NO: 18)
5'-CCCTCGC<u>CCT GAGTACTGTC C</u>CCCGTCCGT CCGGTGAGGG CCACTATCGC TAACTGATCA-3'

Group 2
4
(SEQ ID NO: 19)
5'-AG<u>GCCGTTGG TGTGGTGGGC CTAGGGCCGG CGGCGCACAG CTGTTATAGA CG</u>TCTCCAGC-3'

12-5
(SEQ ID NO: 20)
5'-CC<u>GCCGTTGG TGTGGTGGGC CTAGGGCCGG CGGCGCACAG CTGTTATAGA CG</u>TCTCCAGC-3'

6
(SEQ ID NO: 21)
5'-CC<u>GCCGTTGG TGTGGTGGGC CTAGGGCCGG CGGCGCACAG CTGTTATAGA CG</u>CCTCCAGC-3'

12-7
(SEQ ID NO: 22)
5'-CC<u>GCCGTTGG TGTGGTGGGC C</u>CAGG<u>GCCGG CGGCGCACAG CTGTTATAGA CG</u>CCTCCAGC-3

Group 3
12-2
(SEQ ID NO: 23)
5'-<u>TGACGGTGGC GTGGAGGGCG CGTATCAATC GTTGATCGCA GGGCCGTCAT ACCGTTGGAG</u>-3'

12-9
(SEQ ID NO: 24)
5'-<u>TGACGGTGGC GTGGAGGGCG CGTATCAATC GTTGATCGCA GGGCCGTCAT ACCGTTGGG</u>GG-3'

12-6
(SEQ ID NO: 25)
5'-<u>TGACGGTGGC GTGGAGGGCG CGTATCAATC GTTGATCGCA GGGCCGTCAT ACCG</u>GT<u>CGG</u>G-3'

Group 4
2
(SEQ ID NO: 26)
5'-GCCGACAGGG CATGGGACGC TATCAGCGGT GTC<u>AATCGAA TTCCCGCGGC CG</u>CCATGCGG-3'

14
(SEQ ID NO: 27)
5'-GGTCCCCGCA GCTCATACGG CGCTCCAGCG TA<u>ATCGAATT CCCGCGGCCG</u> CCATGCGGCC-3'

46
(SEQ ID NO: 28)
5'-GCGAGTGGCC CATCAGCAGA GCGTAATCCC CACGCAC<u>ATC GAGTGCCCCC GGCCG</u>GTGCT-3'

Group 5
12
(SEQ ID NO: 29)
5'-<u>GTATTGTCAT TCATATCCTC GTGCTTGCTG TCCTCACCCC ACCCACCAGA ATGG</u>AAA-3'

13
(SEQ ID NO: 30)
5'-CCT<u>GTATTG TCTTGCCAAT CCTCGCCCTG GCTGTCTTAC CCCTCCCCAC CCGCCTGAAG</u>-3'

Group 6
48
(SEQ ID NO: 31)
5'-GTCGACTC<u>GC GGGTACCGTG CT</u>CAATGTCC CAATCCGGGG AAGCGTTTAG ACCCGCAGCC CAC-3'

40
(SEQ ID NO: 32)
5'-GTCGCC<u>ACTG CGGGTACCGT GCT</u>TGGGCNA CCGATGNACC NTGNNACCGT GTTTNGCC-3'

Group 7
3
(SEQ ID NO: 33)
5'-C<u>CGGTGGGTG GTCAGGTGGG ATA</u>GCGTTCC GCGTATGGCC CAGCGCATCA CGGGTTCGCA CCA-3'

-continued

32
(SEQ ID NO: 34)
5'-GGGCGGTGGG TGGCGAGTTG TGAGACGCTG GAGGAGGTTG

CTGCCCCGG CACATTGGGA-3'

In the above sequences, the underlined portions indicate conserved consensus sequences. Specifically, the consensus sequences including the aptamer of each group are as follows: in group 1, 5'-CCTGAGKWACT GYCC-3' (K=G or T, W=A or T, Y=T or C; SEQ ID NO: 1); in group 2, 5'-GCCGTTGG TGTGGTGGGC CYAGGGCCGG CGGCGCACAG CTGT-TATAGA CGYCTCCAGC (Y=C or T; SEQ ID NO: 2); in group 3, 5'-TGACGGTGGC GTGGAGGGCG CGTAT-CAATC GTTGATCGCA GGGCCGTCAT ACCGKTSGRT AC (K=G or T, S=C or G, R=A or G; SEQ ID NO: 3); in group 4, 5'-ATCGARTKCC CSCGGCCT AC (R=A or G, K=G or T, S=C or G; SEQ ID NO: 4); in 5'-G in group 5, 5'TCNT NCNNATTTGA GNNCTNGC5'-TGNT AC (N=A, T, C or G; SEQ ID NO: 5); in group 6, 5'-GCGGGTACCG TGCT AC (SEQ ID NO: 6); and in group 7, 5'-CGGTGGGTGG NNAGNTGNGA NA-3' (N=A, T, C or G; SEQ ID NO: 7).

Example 2

Measurement of the Activity of Bisphenol A 2-1: Measurement of Binding Affinity for Bisphenol A using Real-Time PCR Using real-time PCR, the binding affinities of the following materials for bisphenol A were measured: the initial ssDNA pool before the SELEX process was performed; the eluents (R11 and R12) obtained in rounds 11 and 12; and the aptamers obtained in rounds 11 and 12 (aptamer #3 (SEQ ID NO: 33) and aptamer #6 (SEQ ID NO: 21), obtained in round 11; aptamer #12-3 (SEQ ID NO: 16) and aptamer #12-5 (SEQ ID NO: 20), obtained in round 12). As a control group for the BPA-coupled column, a control column not coupled with BPA was used.

Specifically, each of forward and reverse primers was added to a PCR mix at a concentration of 5 pmol/μl, and then real-time PCR was performed under the following conditions: 2 min at 50° C., then 10 min at 95° C.; then 40 cycles of 15 sec at 95° C., 30 sec at 60° C., and 30 sec at 72° C.; and then 10 min at 72° C. The real-time reaction mixture consisted of 25 ml SYBR Green Mix (2×) (Takara, Japan), 2 ml primer pair mix (5 pmol/ml each primer) (Bioneer, Korea) and 22.5 ml $H_2O$, and the results of the real-time PCR reaction were analyzed using ABI Prism SDS 7000 (Eurogentec, Belgium).

Forward primer:
(SEQ ID NO: 36)
5'-GGGCCGTTCGAACACGAGCATG-3'

Reverse primer:
(SEQ ID NO: 37)
5'-CCTAGGATGACCTGAGTACTGTCC-3'

Figure 2:
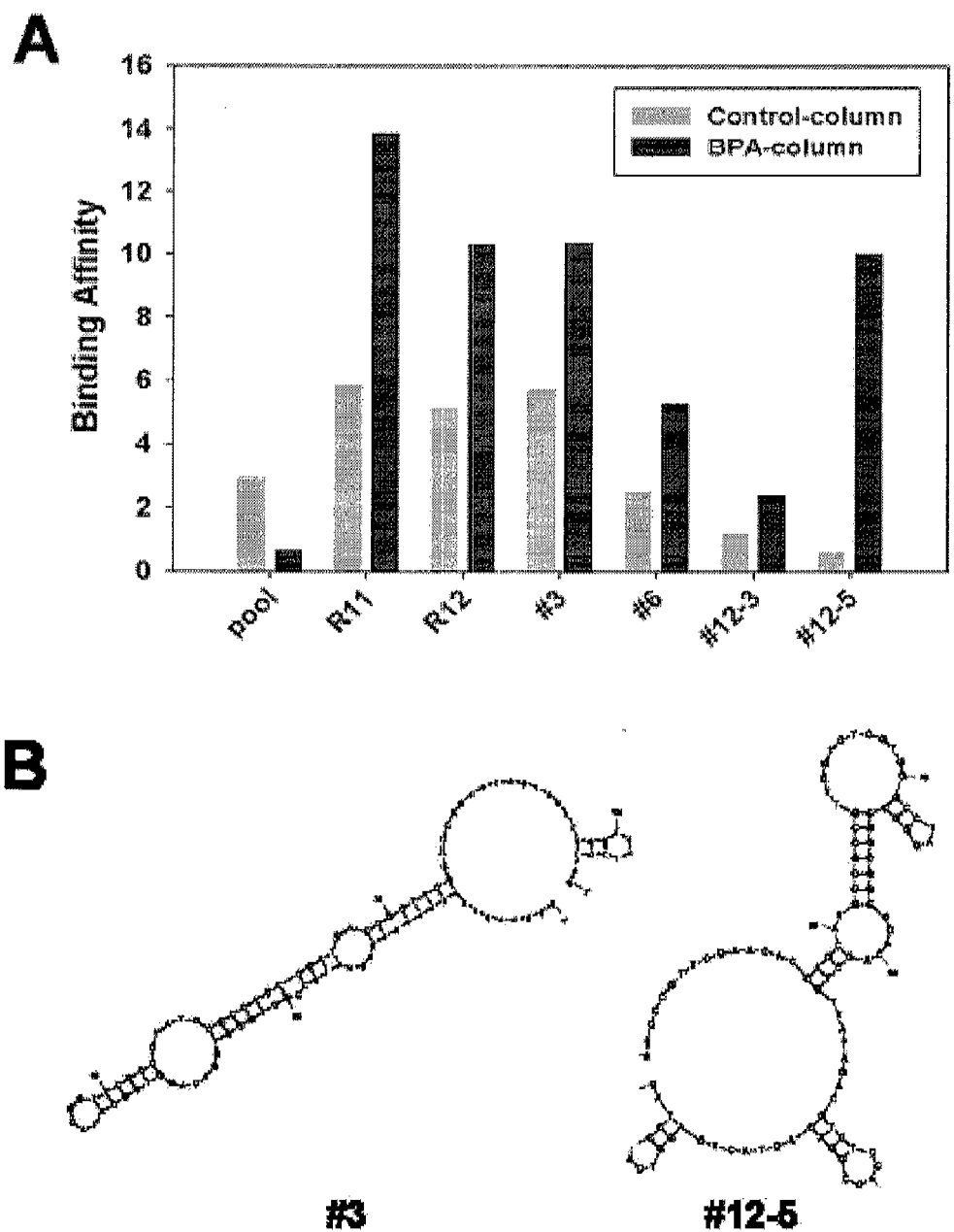
FIG. 2 depicts a graph showing affinities for a bisphenol A-coupled column and a bisphenol A-uncoupled column, analyzed by a real-time PCR assay (FIG. 2A), and shows the secondary structure of selected aptamers (#3 and #12-5) binding specifically to bisphenol A (FIG. 2B).

As a result, as shown in FIG. 2A, aptamer #3 (SEQ ID NO: 33), aptamer #6 (SEQ ID NO: 21), aptamer #12-3 (SEQ ID NO: 16) and aptamer #12-5 (SEQ ID NO: 20) were all shown to have affinity for bisphenol A, and among these, aptamers #3 (SEQ ID NO: 33) and #12-5 (SEQ ID NO: 20) were shown to have particularly high affinity for bisphenol A.

In particular, it was found that aptamer #12-5 (SEQ ID NO: 20) showed very low affinity for the control column while showing very high affinity for bisphenol A, suggesting that it can be used as an effective aptamer for detection and removal of bisphenol A.

Meanwhile, the secondary structures of several aptamers were analyzed through a free energy minimization algorithm using Mfold software available at hypertext transfer protocol: frontend.bioinfo.rpi.edu/applications/mfold/cgi-bin/dna-form1.cgi. The secondary structures of aptamer #3 (SEQ ID NO: 33 and aptamer #12-5 (SEQ ID NO: 20) are shown in FIG. 2B.

2-2: Measurement of Dissociation Constant (Kd) for Bisphenol A by Equilibrium Filtration Method A binding assay was performed using an equilibrium filtration method. To determine dissociation constant (Kd), serial dilutions of folded ssDNA were dissolved in binding buffer containing 75 μM bisphenol A in 200 μl of reaction solution and were incubated at room temperature for 1 hour. The resulting mixtures were loaded into a YM3 Microcon filter column (Amicon) and then centrifuged at 12,000 g for 60 minutes, thus obtaining about 160 μl of each of filtrates.

The solution remaining on the molecular weight cut-off membrane contained both bisphenol A-bound ssDNA and bisphenol A-unbound ssDNA, but the filtrate contained only bisphenol A unbound to ssDNA. The absorbance of the filtrate samples was measured with a spectrophotometer (Biorad) at 278 nm to determine the concentration of bisphenol A.

To calculate dissociation constant, using Sigmaplot 10.0 software and the following equation, the percent of bound bisphenol A versus ssDNA aptamer concentration was plotted, and the data points were fitted into nonlinear regression analysis:

$$y=(B_{max} \cdot ssDNA)/(K_d + ssDNA)$$

wherein y is the degree of saturation, $B_{max}$ is the number of maximum BPA binding sites, and $K_d$ is dissociation constant.

As a result, aptamer #3 (SEQ ID NO: 33) and aptamer #12-5 (SEQ ID NO: 20), shown to have the highest affinity through real-time PCR in Example 2-1, had dissociation constants of 8.3 nM and 230 nM, respectively.

The real-time PCR assay results shown in FIG. 2A indicated that aptamer #12-5 (SEQ ID NO: 20) showed strong affinity, but the dissociation constant results measured using the equilibrium filtration method indicated that aptamer #3 (SEQ ID NO: 33) had the strongest affinity.

In general, the affinity of antibody for a small molecule is very low compared to the affinity of the antibody for a macromolecule. In view of this fact, it is very surprising that the aptamer according to the present invention shows affinity at nM concentration. Namely, it was found that the aptamer according to the present invention showed very strong affinity for bisphenol A.

Example 3

Examination of Aptamer Binding to Bisphenol A using Sol-Gel Chip

Figure 3:
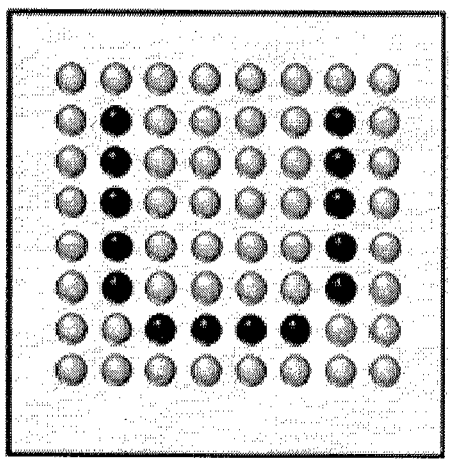
FIG. 3 shows the results of analyzing the binding between bisphenol A and aptamer #3 using a three-dimensional sol-gel chip.
Figure 3:
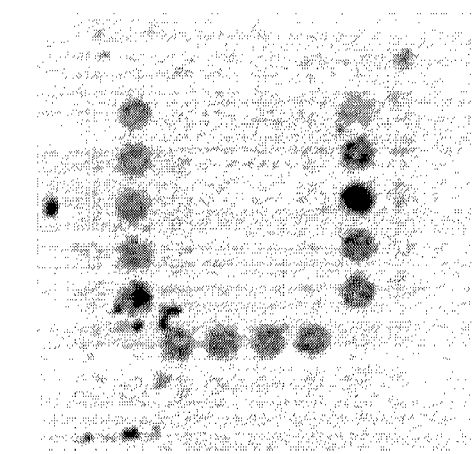

In order to assess the affinities of the selected aptamers for bisphenol, a sol-gel chip was prepared. First, as shown in FIG. 3, a negative control (◎) and bisphenol A (●) were spotted on a surface-modified silicon surface using sciFLEXAR-RAYER (Scienion, Germany) and immobilized by gelation, thus making sol-gel spots.

A sol composition used to make the sol-gel spots as described above was prepared in the following manner. Tetramethyl orthosilicate (TMOS) and methyltrimethoxysilicate (MTMS) were mixed with each other to prepare a sol composition. Also, as solution I, 10 mM HCl was prepared.

Meanwhile, 10 μl of 10 mM SP buffer (pH 5.8) and 20 μl of double-distilled water (DDW) were mixed with each other. For a test group, 10 μl of bisphenol A was added to the mixture, after which the resulting mixture was vortexed for 5 seconds and spun-down, thus preparing solution II. For a negative control, only buffer was used.

Thereafter, aptamer #3 was labeled with Cy3, using terminal deoxynucleotidyl transferase (Fermentas, Canada) and Cy3-dUTP (GeneChem, Korea). The sol-gel spots were gelled for 13-15 hours, after which 2 μM of the Cy3-labeled aptamer was added to each well, and the aptamer bound to the sol-gel spots was assayed. Then, each well was washed, and the assayed spots were observed with a FLA5100 fluorescence scanner (FUJIFILM, Japan) and analyzed with a Multi-image analyzer and Multi-gauge program.

The analysis results are shown in FIG. 3. As can be seen therein, signals appeared only in the chips immobilized with bisphenol A, suggesting that the aptamer according to the present invention can specifically detect bisphenol A.

Example 4

Detection of Bisphenol A in Sol-Gel Chip using Bisphenol A-Specific Aptamer

Figure 4:
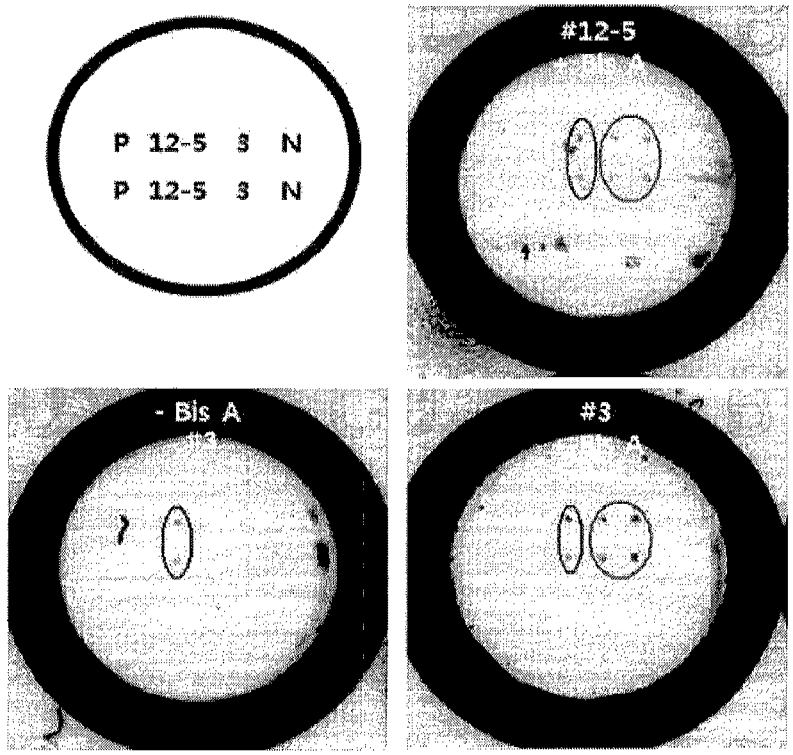
FIG. 4 shows the results of performing a sandwich assay of two bisphenol A-specific aptamers #3 and #12-5 in a three-dimensional sol-gel chip.

To assess the affinity of the selected aptamers for bisphenol A, a sol-gel chip was prepared. First, as shown in FIG. 4, a positive control (P), aptamer #12-5, aptamer #3 and a negative control (N) were sequentially spotted on a PMMA-coated 96-well plate using OmniGrid Accent Microarrayer (DIGI LAB, USA) and immobilized by gelation to make sol-gel spots.

A composition used to make the sol-gel spots as described above was prepared in the following manner. Tetramethyl orthosilicate (TMOS) and methyltrimethoxysilicate (MTMS) were mixed with each other to prepare a sol composition. As solution I, 100 mM HCl was prepared.

Meanwhile, 100 mM SP buffer (pH 5.8) and 20 μl of double-distilled water (DDW) were mixed with each other. For a positive control, 10 μl of Cy3 antibody (Santa Cruz, USA) was added to the mixture, and for test groups, 10 μl of each of the selected aptamers (aptamers #3 and #12-5) was added to the mixture. Then, each of the mixtures was vortexed for 5 seconds and spun-down, thus preparing solution II. For a negative control, only buffer was used.

Thereafter, each of aptamers #3 and #12-5 was labeled with Cy3, using terminal deoxynucleotidyl transferase (Fermentas, Canada) and Cy3-dUTP (GeneChem, Korea). The sol-gel spots were gelled for 13-15 hours, after which 50 μM of bisphenol A and 2 μM of the cy3-labeled aptamer were added to each well and subjected to sandwich assay. Specifically, as shown in FIG. 4, the well shown on the upper right side of FIG. 4 was treated with bisphenol A (BPA) and aptamer #12-5, the well on the lower left side with buffer and aptamer #3, and the well on the lower right side with BPA and aptamer #3, and each well was incubated. Then, each well was washed, and the assayed spots were observed with a FLA5100 fluorescence scanner (FUJIFILM, Japan) and analyzed with a Multi-image analyzer and Multi-gauge program.

The analysis results are shown in FIG. 4. As can be seen therein, only in the case in which bisphenol A was present, signals (indicated by red circles) appeared at the positions where aptamers #12-5 and #3 were immobilized, suggesting that the aptamer according to the present invention can specifically detect bisphenol A.

Example 5

Measurement of Affinities for Bisphenols Other than Bisphenol A

Figure 5:
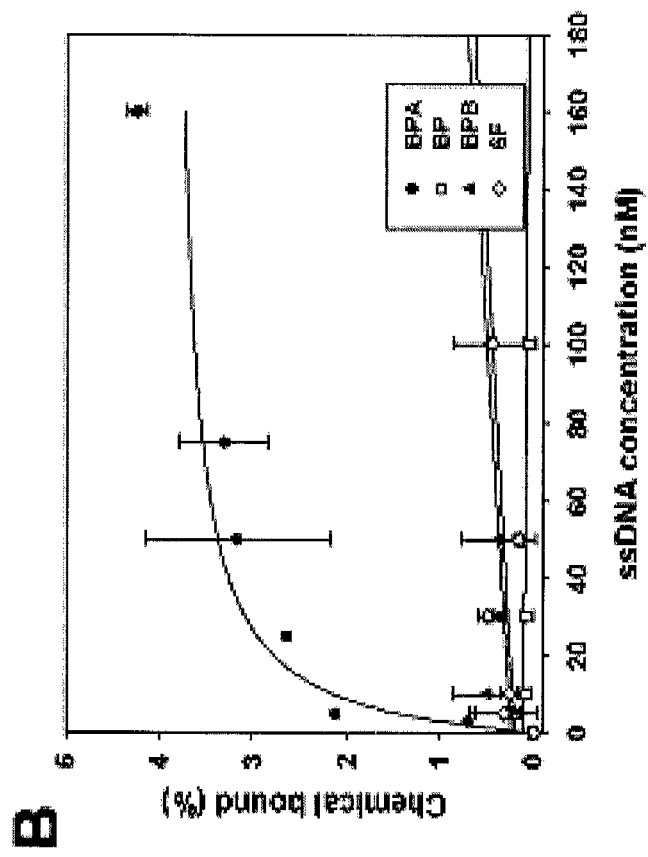
FIG. 5 shows the structural formulas of bisphenol A and other bisphenols (FIG. 5A) and a graph showing the affinity of bisphenol A-specific aptamer #3 for each of the bisphenol compounds (FIG. 5B).
Figure 5:
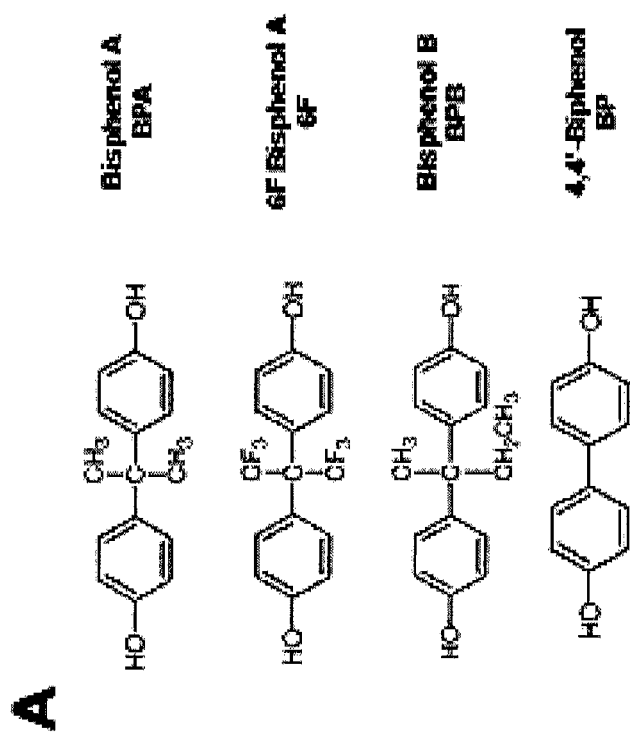

In order to confirm whether the aptamer of the present invention binds specifically to bisphenol A, the affinities ((Kd) of aptamer #3 (SEQ ID NO: 33) for other bisphenols having structures similar to that of bisphenol A, for example, bisphenol B (BPB), 4,4'-bisphenol (BP) and bisphenol A (6F), shown in FIG. 5A, were measured according to the method of Example 2-2.

The measurement results are shown in FIG. 5B. As can be seen therein, aptamer #3 showed dissociation constants of 0.8 nM for bisphenol A, 208 nM for 6F, 139 Mm for BPB, and 139 mM for BP, indicating that aptamer #3 binds specifically only to bisphenol A.

Although BPB shown in FIG. 5A has no difference bisphenol A except for a single methyl group, aptamer #3 showed no affinity for BPB and showed specific affinity only for bisphenol A.

Example 6

Figure 6:
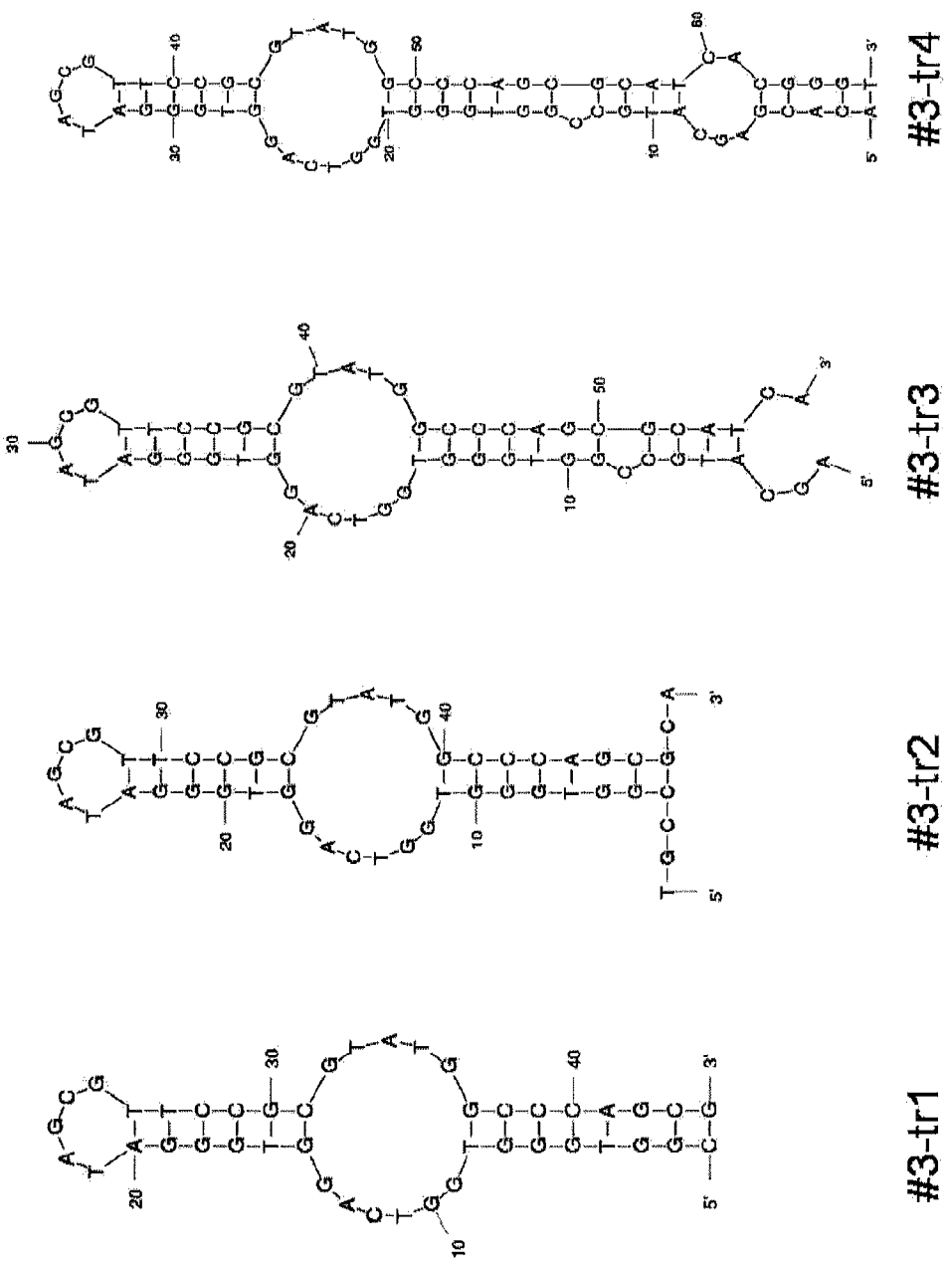
FIG. 6 shows the structures of trimmed forms of aptamer (#3-tr1, #3-tr2, #3-tr3 and #3-tr4).

Analysis of Binding Affinities of Trimmed Forms of Aptamer #3 for Bisphenol A by Equilibrium Filtration Method In order to examine the binding affinity of a trimmed form of aptamer #3 (SEQ ID NO: 33) for bisphenol A, a binding assay was performed by the equilibrium filtration method. Specifically, trimmed forms of aptamer #3 (#3-tr1, #3-tr2, #3-tr3 and #3-tr4), set forth in SEQ ID NO: 38 to SEQ ID NO: 41 and having the structures shown in FIG. 6, were constructed.

3-tr1:
(SEQ ID NO: 38)
5'-CGGTGGGTGGTCAGGTGGGATAGCGTTCCGCGTATGGCCCAGCG-3'

3-tr2
(SEQ ID NO: 39)
5'-TGCCGGTGGGTGGTCAGGTGGGATAGCGTTCCGCGTATGGCCCAGC

GCA-3'

3-tr3
(SEQ ID NO: 40)
5'-AGCATGCCGGTGGGTGGTCAGGTGGGATAGCGTTCCGCGTATGGCC

CAGCGCATCA-3'

3-tr4
(SEQ ID NO: 41)
5'-ACACGAGCATGCCGGTGGGTGGTCAGGTGGGATAGCGTTCCGCGTA

TGGCCCAGCGCATCACGGGT-3'

Each of dilutions of the trimmed forms of aptamer #3 (#3-tr1, #3-tr2, #3-tr3 and #3-tr4) was dissolved in binding buffer containing 75 μM of bisphenol A in 200 μl of a reaction solution and incubated at room temperature for 1 hour. As a control, a solution of bisphenol A alone in binding buffer was used. Each of the resulting mixtures was loaded into a YM3 Microcon filter column (Amicon), and then centrifuged at 12,000 g for 60 minutes, thus obtaining about 150 μl of each of filtrates. The solution remaining on the molecular weight cut-off membrane contained both bisphenol A-bound ssDNA and bisphenol A-unbound ssDNA, but the filtrate contained only bisphenol unbound to ssDNA. The absorbance of the filtrate samples was measured using a spectrophotometer (Bio-rad) at 276 nm, thus determining the concentration of bisphenol A in the filtrate samples. The ratio of the binding of bisphenol A to each of the trimmed aptamer forms relative to the control group was calculated, and the calculation results were graphically shown.

Figure 7:
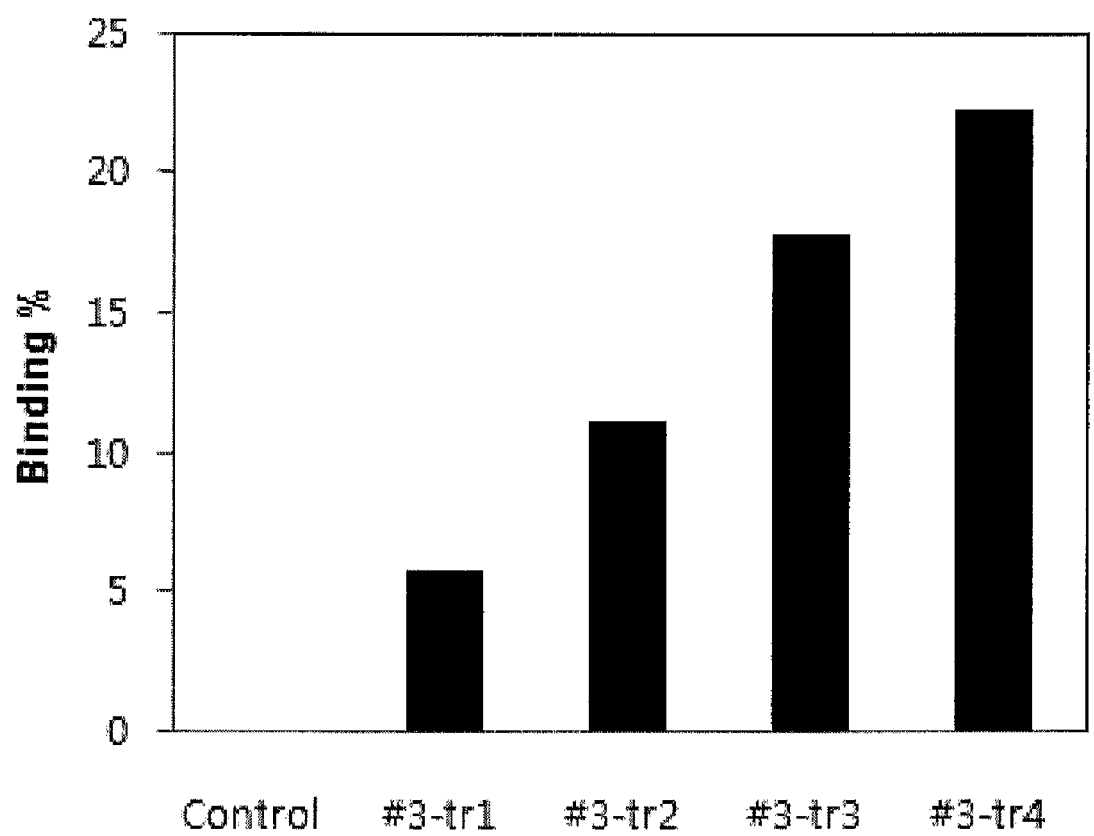
FIG. 7 is a graph showing the results of analyzing the binding of trimmed forms of aptamer (#3-tr1, #3-tr2, #3-tr3 and #3-tr4) to bisphenol A.

As a result, as shown in Table 1 below and FIG. 7, the ratio of binding of bisphenol A to each of the trimmed aptamer forms was 5.8% for #3-tr1, 11.1% for #3-tr2, 17.9% for #3-tr3, and 22.3% for #3-tr4. Namely, trimmed aptamer form #3-tr4 showed the strongest affinity for bisphenol A.

TABLE 1

|  | Control group | #3-tr1 | #3-tr2 | #3-tr3 | #3-tr4 |
| --- | --- | --- | --- | --- | --- |
| Filtrate (µl) | 150 | 142 | 155 | 140 | 143 |
| Filtrate OD 276 nm | 0.200 | 0.199 | 0.172 | 0.176 | 0.163 |
| Binding % | 0 | 5.806667 | 11.13333 | 17.86667 | 22.30333 |

INDUSTRIAL APPLICABILITY

As described above, the present invention provides a nucleic acid aptamer capable of binding specifically to bisphenol A and a method of detecting and removing bisphenol A using the same.

The inventive nucleic acid aptamer capable of binding specifically to bisphenol A has affinity for bisphenol A at nM concentration, and thus can detect even a very small amount of bisphenol A. Also, the nucleic acid aptamer can specifically detect only bisphenol A without showing affinity for other bisphenols, including bisphenol B having no difference from bisphenol A except for a single methyl group. Accordingly, the nucleic acid aptamer is effective in detecting and removing the environmental hormone bisphenol A which is difficult to detect by conventional methods.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

Sequence Listing

The electronic file was attached.

What is claimed is:

1. A nucleic acid aptamer capable of binding specifically to bisphenol A, which comprises any one of SEQ ID NO:8 to SEQ ID NO:34 and SEQ ID NO:38 to SEQ ID NO:41.

2. A method for detecting bisphenol A using the nucleic acid aptamer according to claim 1.

3. The method according to claim 2, wherein bisphenol A is detected in a sample taken from at least one of water, soil, air, food, waste, animal and plant organs, and animal and plant tissues.

4. A composition for detecting bisphenol A, which contains the nucleic acid aptamer according to claim 1.

5. A sensor for detecting bisphenol A, which contains the nucleic acid aptamer according to claim 1.

6. A kit for detecting bisphenol A, which contains the nucleic acid aptamer according to claim 1.

7. A method for removing bisphenol A from a composition comprising contacting the composition with the nucleic acid aptamer according to claim 1.

8. A composition for removing bisphenol A, which contains the nucleic acid aptamer according to claim 1.

* * * * *